(12) United States Patent
Kramer

(10) Patent No.: US 6,922,241 B2
(45) Date of Patent: Jul. 26, 2005

(54) FIBER OPTIC APPARATUS FOR DETECTING LIGHT SCATTER TO DIFFERENTIATE BLOOD CELLS AND THE LIKE

(75) Inventor: Donald L. Kramer, Boca Raton, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 10/914,388

(22) Filed: Aug. 9, 2004

(65) Prior Publication Data

US 2005/0007589 A1 Jan. 13, 2005

Related U.S. Application Data

(62) Division of application No. 10/227,003, filed on Aug. 23, 2002, now Pat. No. 6,798,508.

(51) Int. Cl.[7] .......................... G01N 15/02; G01N 33/48
(52) U.S. Cl. ....................... 356/338; 356/340; 356/342; 422/82.05; 422/82.09; 436/164
(58) Field of Search .................. 356/335–343, 356/39, 40; 250/574; 422/73, 82.01, 82.02, 82.05, 82.09; 436/8, 10, 164, 149–150; 435/2

(56) References Cited

U.S. PATENT DOCUMENTS

| | | | |
|---|---|---|---|
| 3,835,315 A | 9/1974 | Gravitt | |
| 4,175,865 A | 11/1979 | Horvath et al. | |
| 4,497,577 A | 2/1985 | Sato et al. | |
| 4,595,291 A * | 6/1986 | Tatsuno | 356/336 |
| 4,702,598 A | 10/1987 | Bohmer | |
| 4,710,025 A * | 12/1987 | Wyatt et al. | 356/343 |
| 4,914,310 A | 4/1990 | Jarofski | |
| 5,012,119 A * | 4/1991 | Rhiner | 250/574 |
| 5,125,737 A | 6/1992 | Rodriguez et al. | |
| 5,461,476 A | 10/1995 | Fournier | |
| 6,137,108 A | 10/2000 | DeThomas et al. | |
| 6,232,125 B1 | 5/2001 | Deka et al. | |
| 6,743,634 B2 * | 6/2004 | Kramer | 436/63 |
| 6,798,508 B2 * | 9/2004 | Kramer | 356/338 |
| 6,869,569 B2 * | 3/2005 | Kramer | 422/73 |
| 2004/0036875 A1 * | 2/2004 | Kramer | 356/342 |

OTHER PUBLICATIONS

Eisert, W.G., "Cell Differentiation Based on Absorption and Scattering", The Journal of Histochemistry and Cytochemistry, vol. 27, No. 1, pp. 404–409 (1979).

* cited by examiner

*Primary Examiner*—Hoa Q. Pham
(74) *Attorney, Agent, or Firm*—Warren W. Kurz; Mitchell E. Alter

(57) ABSTRACT

Apparatus for detecting light scattered by a small particle (e.g., a blood cell) irradiated by a light beam comprises one or more photodetectors and a plurality of optical fibers that serve to optically couple the scattered light and the photodetector(s). To enhance the efficiency of such optical coupling, a portion of each of the optical fibers in the vicinity of its light-collecting end is supported so that its optical axis extends towards the light-scattering source. By this arrangement, scattered light enters each fiber from a direction substantially parallel to the fiber axis. Preferably, the light-collecting ends of the optical fibers are supported on a concave surface and so that the respective optical axes of the fibers converge at a point representing the apparent position of the light-scattering source, taking into account the refractive effects of an optical flow cell through which scattering is detected. Preferably, both forward- and back-scattered light are detected by the apparatus of the invention.

9 Claims, 8 Drawing Sheets

FIBER OPTIC APPARATUS FOR DETECTING LIGHT SCATTER TO DIFFERENTIATE BLOOD CELLS AND THE LIKE

RELATED U.S. APPLICATION DATA

Division of U.S. application Ser. No. 10/227,003 filed Aug. 23, 2002, now U.S. Pat. No. 6,798,508, entitled "Fiber Optic Apparatus for Detecting Light Scatter to Differentiate Blood Cells and the Like".

CROSS REFERENCE TO RELATED APPLICATIONS

Reference is made to the following commonly assigned U.S. patent applications in the name of Donald L. Kramer. The respective disclosures of these applications are incorporated herein by reference:

(1) U.S. application Ser. No. 10/227,004 filed Aug. 23, 2002, entitled "Apparatus for Detecting Back-Scatter in a Laser-Based Blood Analysis System."

(2) U.S. application Ser. No. 10/227,010 filed Aug. 23, 2002 (now U.S. Pat. No. 6,743,634 granted Jun. 1, 2004), entitled "Method and Apparatus for Differentiating Blood Cells Using Back-Scatter."

FIELD OF THE INVENTION

The present invention relates to improvements in apparatus for differentiating small particles of various types on the basis of their respective light scattering characteristics. The invention is particularly useful in hematology instruments for differentiating various types or classes of blood cells.

BACKGROUND OF THE INVENTION

The use of light scattering measurements as a means for differentiating various types of small particles is well known. For example, in virtually all sophisticated hematology instruments, it is common to measure the forward light scattering properties of blood cells by passing the cells, one at a time, through the interrogation zone of an optical flow cell. While in the interrogation zone, each cell is irradiated by a laser beam, and one or more photodetectors, strategically positioned forward of the interrogation zone, operate to sense the level of forward scattered radiation, often within different predetermined angular ranges. In addition to measuring forward light scatter, some hematology instruments measure side scatter as well, using a separate photodetector located laterally of the irradiated cell. These light scattering measurements are often combined with other simultaneously made measurements, e.g., axial light-loss, DC volume and/or RF conductivity measurements, to better differentiate cell types of particular interest from other cells and particulate material in the sample that have similar light-scattering properties within the measurement ranges. Having made the various parameter measurements, the instrument then produces scattergrams in which the different parameters measured are plotted against each other. Ideally, each cell type appears on these scattergrams as a tight cluster of data points, each point representing an individual cell, and each cluster being readily identifiable by a clearly identified spacing from other clusters of data points. In such case, it is a relatively simple matter to "gate" cells of one cluster from those of another cluster and to enumerate the cells of each type. This ideal, unfortunately, is sometimes difficult to realize since, for a variety of reasons, a certain percentage of cells of one type invariably invade the spatial domain of cells of other types, making the differentiation of each type somewhat imprecise.

To more precisely differentiate blood cells and the like on the basis of their light-scattering signature, various photodetector configurations have been proposed. As noted above, it is often desirable to measure light scatter within different angular ranges. To effect such measurements, some photodetectors comprise a series of concentric rings or, more commonly, ring segments of light-sensitive material, typically PIN diode material. The rings or segments thereof are positioned in a plane forward of the cell interrogation zone with the ring center coinciding with the axis of the cell-irradiating beam. The spacing between the detector plane and the interrogation zone, together with the radial position and width of each ring determines the angular range within which forward light scatter is measurable. Such a photodetector configuration is disclosed, for example, in U.S. Pat. No. 6,232,125 to Deka et al. In such a detector configuration, the area of the light-sensitive material of each detector ring or arc increases with ring diameter. So, too, does the sensitivity of the ring due to the increased area of the photodetector material. This increased sensitivity is desirable from the standpoint that the light scatter intensity (on average) decreases dramatically with increasing scatter angle. But, the increasing detector size from ring to ring with increasing angle results in an undesirable decrease in detector response time, the latter being inversely proportional to the detector's active area.

It has been suggested that multiple bundles of fiber optics, arranged in concentric rings, can be used to optically couple scattered radiation from a scatter plane to multiple photodetectors (e.g., photomultiplier tubes and photodiodes) remotely spaced from the scatter plane. See, "Cell Differentiation Based on Absorption and Scattering" by Wolfgang G. Eisert, The Journal of Histology and Cytochemistry, Vol. 27, No. 1, pp. 404–409 (1979). As described by Eisert, optical fibers are arranged so that their respective light-collecting ends form five concentric rings centered about a centrally located light-collecting bundle of optical fibers. The respective distal ends of the individual fibers of each of the five concentric rings are optically coupled to five different photomultiplier tubes, and the distal ends of the individual fibers of the center bundle are optically coupled to a photodiode. Thus, each ring of fibers collects scattered light in a discrete angular range determined by the diameter of the fiber (or the width of the rings), the radial displacement of the fiber end relative to the beam axis, and the axial spacing of the fiber ends from the scattering light source. The center bundle of fibers is optically aligned with the beam axis, and the other bundles, with their individual fibers being arranged in a circle, are also arranged parallel to the beam axis. The center bundle of fiber optics, being positioned on the beam axis, serves to monitor the axial light loss of the beam, as occasioned by the passage of cells therethrough.

In the fiber-optic light coupler proposed by Eisert above, the respective light-collecting ends of all the fibers are disposed in a common plane that is arranged perpendicular to the optical axis of the cell-irradiating light beam. Thus, it will be appreciated that, due to the numerical aperture of the fibers, the optical coupling of scattered light into the optical fibers deteriorates as the scatter angle increases. Additionally, as the scatter angle increases, the angle of incidence between the scattered light and the fiber end increases, thereby increasing the number of internal reflections required to transmit the scattered light from one end of the fiber to the other end. This problem of coupling efficiency is exacerbated by the dramatic reduction in scatter intensity at relatively large scatter angles. Further, the presence of the respective fiber ends of the central bundle of fibers in the scatter-detection plane can be problematic from a retro-reflection standpoint, i.e., the fiber ends tend to reflect a significant percentage of the relatively intense cell-irradiating light beam backwards, towards the optical flow cell used to control the movement of cells. Upon being reflected again by the flow cell surface, the re-reflected light will be collected by the fiber ends surrounding the central bundle, the result being that the relatively low level light scatter signals from the cells of interest are swamped out.

SUMMARY OF THE INVENTION

In view of the foregoing discussion, an object of this invention is to provide an apparatus for more efficiently coupling light scattered from, or otherwise modulated by, an irradiated particle (e.g., a blood cell) to a photodetector in an apparatus adapted to differentiate such particles on the basis of their respective light-scattering signatures.

In accordance with a preferred embodiment of the invention, apparatus for detecting light scatter from an irradiated particle of interest comprises (a) an optically transparent flow cell having a cell-interrogation zone through which particles of interest can be made to pass, one at a time, while a beam of optical radiation irradiates each particle; and (b) a plurality of optical fibers that operate to receive scattered light from the irradiated particles and to transmit such light, via multiple internal reflections, to one or more remote photodetectors for detection. According to the invention, a portion of each fiber in the vicinity of its light-collecting end is supported so that the optical axis of the supported fiber portion extends towards the scattering source (i.e., the irradiated particle), and most preferably towards the apparent position of the scattering source, taking into account the refractive effects of the optical flow cell wall through which the light scatter is collected. As a result of this arrangement, the scattered light is efficiently coupled into the fibers and transmitted through the fibers with minimal losses. Preferably, one end of each optical fiber (i.e., its light-collecting end) is disposed on a spherically-concave surface of an optical fiber holder that serves to optimally position the fibers for light-collection. In use, the concave surface is arranged so that its center of curvature is located proximate the apparent position of the light-scattering particles, again as viewed through an optically transparent wall of the optical flow cell. Preferably, the light-collecting optical fiber ends are arranged on the concave surface to form one or more circular or arcuate patterns with the center of the circle(s) or arcs coinciding with the axis of the particle-irradiating beam. Preferably, additional optical fibers are supported by the fiber optic holder in positions to collect axial beam light as modulated in intensity by particles passing through the beam path, and as diffused by a light-diffusing surface within the fiber optic holder that minimizes retro-reflection of the beam light into regions that may degrade the signal-to-noise level of the detected light signals.

The invention and its advantages will be better understood from the ensuing detailed description of preferred embodiments, reference being made to the accompanying drawings in which like reference characters denote like parts.

DETAILED DESCRIPTION OF PREFERRED EMBODIMENTS

Figure 1:
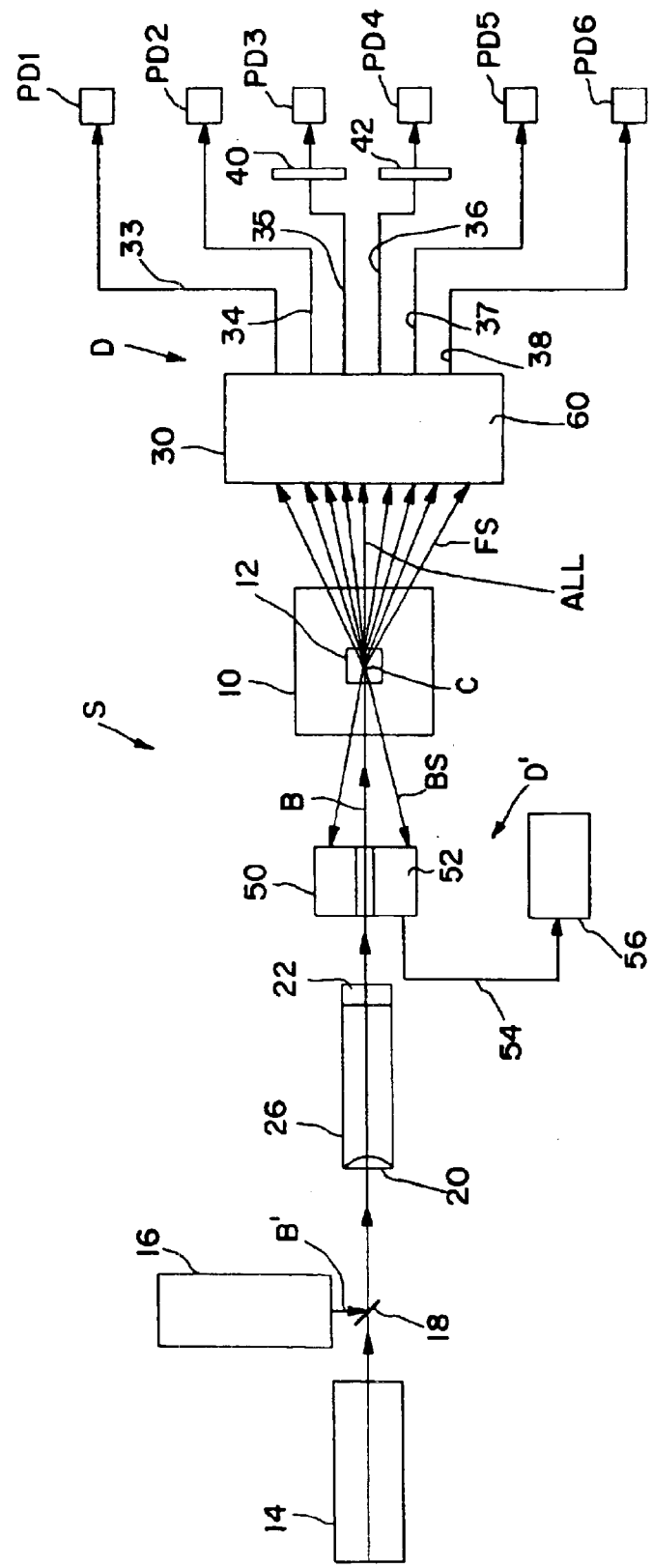
FIG. 1 is a schematic illustration of a portion of a system used to analyze blood cells and other small particles on the basis of the light-scattering signature of such cells and particles.

Referring now to the drawings, FIG. 1 schematically illustrates an electrooptical system S for detecting light scattered by small particles, e.g., blood cells, irradiated by a collimated light beam. As indicated above, systems of this general type are commonly used in hematology instruments for differentiating different types of blood cells in a liquid sample. Central to this particular system is an optical flow cell 10 having a centrally located particle-interrogation zone 12 through which a stream of individual particles of interest in suspension can be made to pass, one at a time, in a well known manner. The flow cell is optically transparent, preferably being fabricated from quartz, and the interrogation zone measures about 100×100 microns in transverse cross section. While passing through the interrogation zone, the individual particles are irradiated by a light beam B provided by a laser 14. Preferably, a second laser 16 is used to provide a second light beam B' that becomes co-linear with beam B after striking the 45 degree, semi-transparent mirror 18. Preferably, the two beams are of different wavelength, for example, one beam being red in color, as provided, e.g., by a helium-neon laser, and the other beam being blue in color, as provided, e.g., by an argon laser. Upon passing through a small aperture formed in the light-collecting optical system comprising a back-scatter detector D' (described below), the beam(s) are brought into sharp focus at the center C of the particle-interrogation zone 12 by a pair of crossed cylindrical lens 20, 22 supported at opposite ends of a lens housing 26. When irradiated by the focused beam(s), each particle acts to scatter light in all directions according to a complex function based upon the wavelength of the irradiating light beam and certain particle characteristics, including size, refractive index, reflectivity, geometry, internal make-up, etc. Further, each irradiated particle acts to modulate the intensity of the irradiating beam(s), again depending on the physical and optical properties of the particle. Forward light scatter FS, i.e., the light scattered forwardly of the irradiated particle, as determined by the direction of propagation of the particle-irradiating beam, is detected within a plurality of different angular ranges by a forward-scatter/axial light-loss detector D, described in detail below. As its name suggests, detector D also operates, as described in detail below, to detect the axial light loss (ALL) in the irradiating beam(s) (sometimes referred to as "zero angle scatter") as occasioned by the passage of a particle through the beam(s). Preferably, such axial light loss is detected at different wavelengths, as determined by the respective radiant outputs of lasers 14 and 16. Back-scattered light BS, i.e., light scattered backwardly or reflected from the irradiated particles toward the irradiating source, is detected within a predetermined angular range by the above-mentioned back-scatter detector D'. Preferred details of the back-scatter detector D' are also described below.

Figure 2:
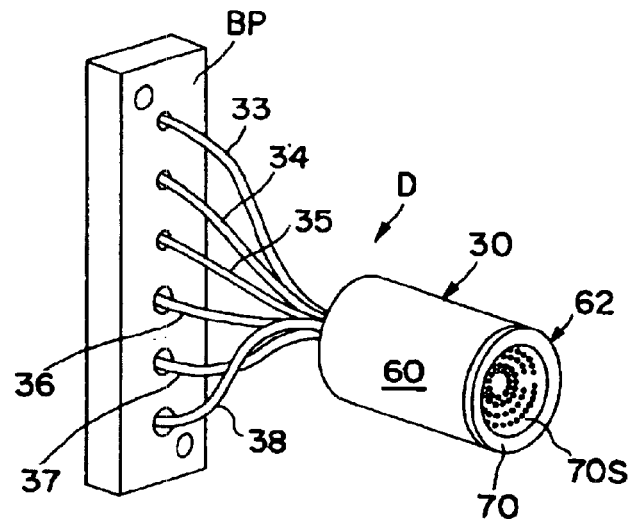
FIG. 2 is a perspective illustration of a portion of a forward light scatter detector structured in accordance with the present invention.

Forward-Scatter/Axial Light-Loss Detector:

Still referring to FIG. 1 and in accordance with the present invention, the forward-scatter/axial light loss detector D generally comprises (i) an optical fiber holder 30, (ii) a plurality of discrete fiber optic bundles 33–38 (illustrated as being six in number, though there may be more or less), and (iii) a like plurality of photodetectors PD1–PD6. The photodetectors may be conventional photomultiplier tubes, solid state devices or any combination of the two. Each fiber optic bundle preferably comprises at least three or four optical fibers and may comprise upwards of fifty fibers, depending on the pattern in which they are arranged within the fiber holder 30, and the diameter of the fibers. Each optical fiber has a light-collecting end that, in use, is positioned to collect or receive radiant energy that is to be transferred by the fiber, via multiple internal reflections, to a relatively remote location, and an opposing light-discharge end that emits the collected and transmitted light. Referring to FIG. 2, a backplate BP serves to support, in suitably sized holes arranged in a vertical array, the light-discharge ends the six fiber optic bundles 33–38. The six photodetectors PD1–PD6 are also supported by plate BP (on the rear side, as viewed in FIG. 2) in a position to receive the light emitted by the respective light-discharge ends of the optical fibers. Preferably, all of the individual fibers in the fiber optic bundles are the same in all respects except, perhaps, for length, which may vary slightly from bundle to bundle, depending on space constraints. Preferably, each fiber has a diameter of about 500 microns, and all fibers are made from a common optical material. Particularly preferred fibers are the SI Bare Fibers, sold by Boston Optical Fiber.

Figure 3:
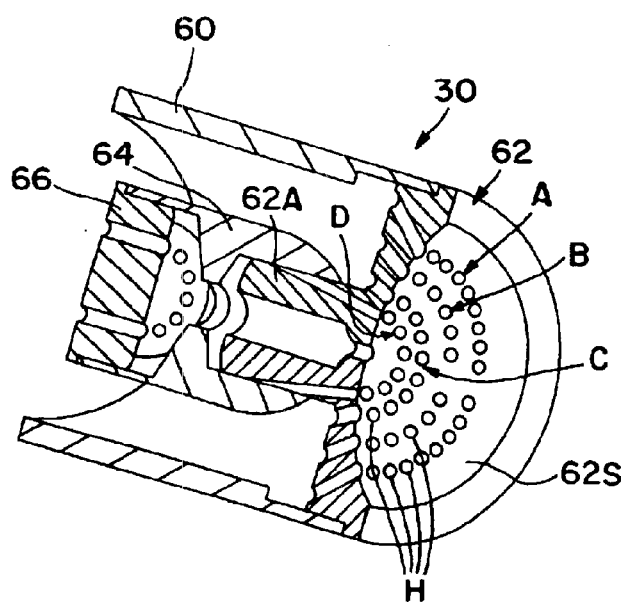
FIG. 3 is an enlarged perspective of a section the light-gathering component of the FIG. 2 apparatus.
Figure 4:
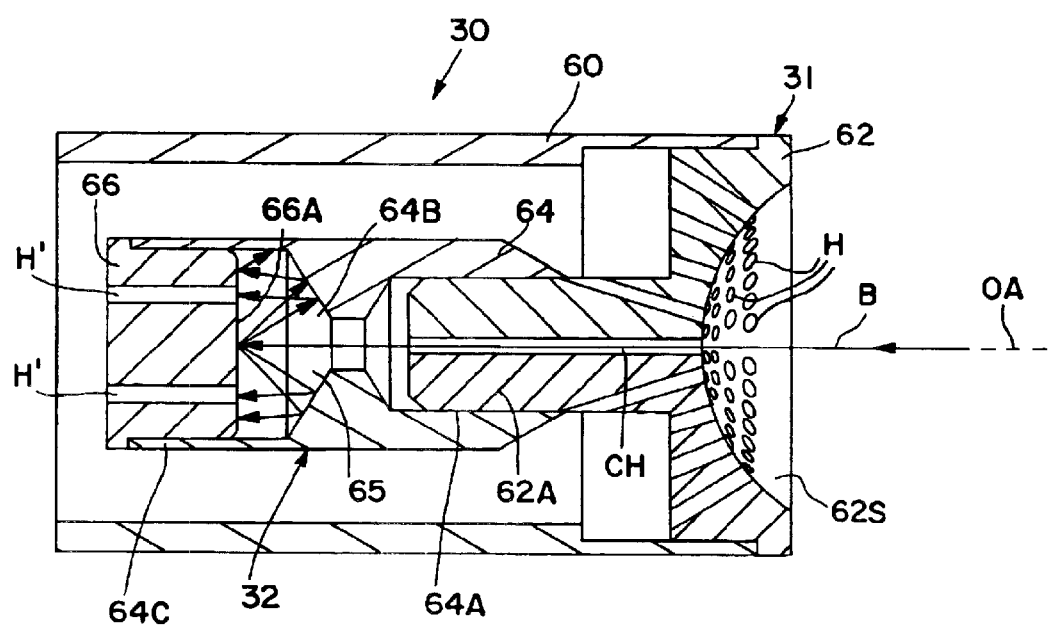
FIG. 4 is a sectional illustration of the FIG. 3 apparatus.

As best shown in FIGS. 3 and 4, optical fiber holder 30 comprises a cylindrical sleeve 60 that serves to support and contain two inter-connected components, namely, (1) a forward light-scatter collecting component 31 that functions to support the respective light-collecting ends of four of the fiber optic bundles in a position to collect forwardly scattered light FS within four different angular ranges, and (2) an axial light-collecting component 32 that functions to support the light-collecting ends of the remaining two fiber optic bundles in a position to collect axial light as modulated in intensity by particles in its path. According to a preferred embodiment, sleeve 60 is made of plastic, has a diameter of about 12.5 mm and has a length of about 20 mm.

Forward Light-Scatter Collecting Component:

The forward light-scatter collecting component 31 of fiber optic holder 30 is positioned within sleeve 60 forwardly of the axial light-collecting component 32. Component 32 functions to hold the respective light-collecting ends of fiber optic bundles 33, 34, 37 and 38 so as to form four concentric rings A, B, C and D, respectively (shown in FIG. 5B). When the fiber optic holder is in use, each ring of fiber optic ends is centered about the optical axis OA of the irradiating beam(s) and functions to collect forwardly scattered light in a discrete angular range determined by the ring diameter, the axial spacing between the scattering source and the fiber end, and the diameter of the fiber. As described above, the light-discharge ends of the bundles 33, 34, 37 and 38 are optically coupled to photodetectors PD1, PD2, PD5 and PD6 in such a manner that each photodetector receives light from only one bundle. Thus, the output of each photodetector reflects the intensity of forwardly scattered light within one of four different angular ranges determined by the position in which the light-collecting ends of the fibers to which it is optically coupled are supported.

Figure 5A:
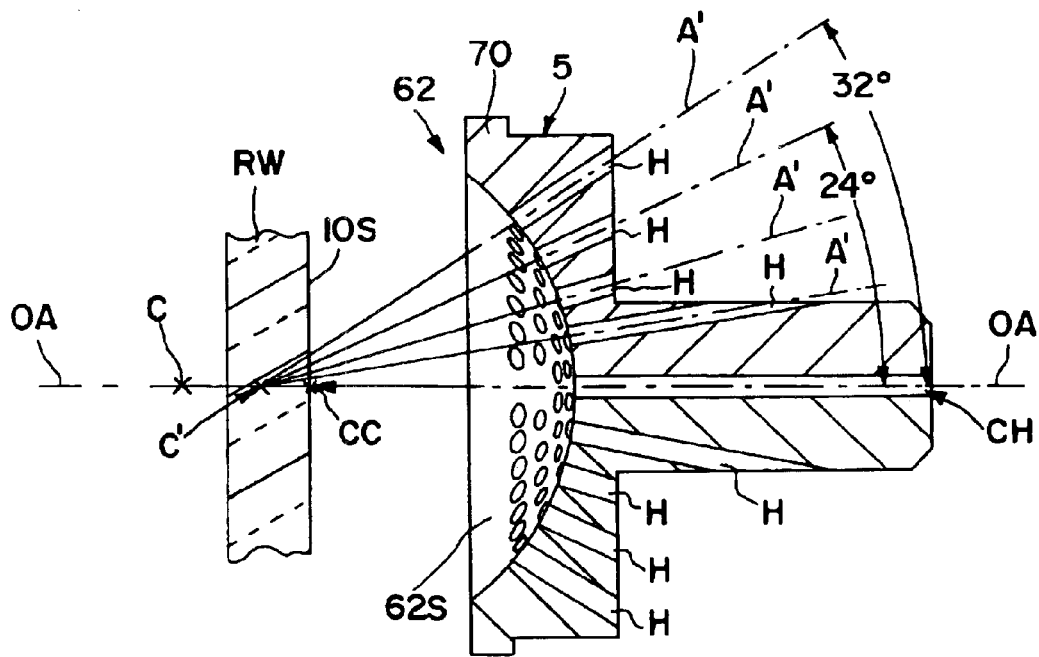
FIGS. 5A and 5B are cross-sectional and front plan views, respectively, of the primary fiber-optic holder component of the FIG. 3 apparatus.
Figure 5B:
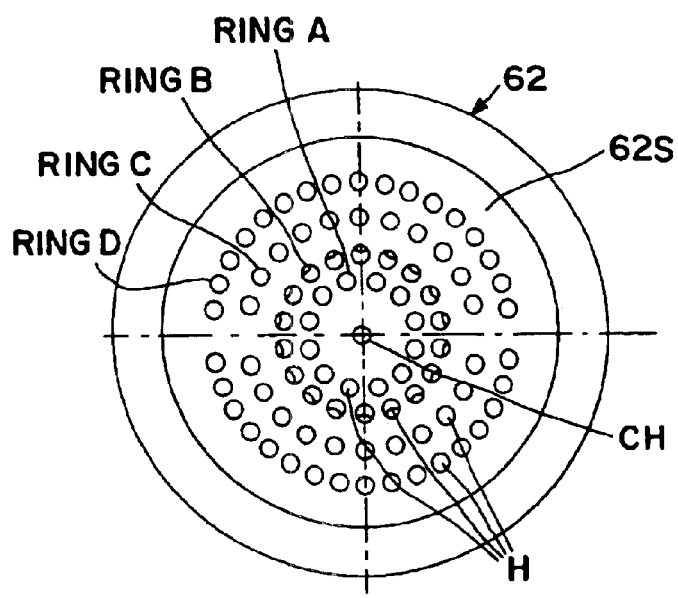

As best shown in FIGS. 3 and 4, the forward light-scatter collecting component 31 comprises a circular, fiber-holding plate 62 having a cylindrical stem potion 62A extending rearwardly from the central region of the plate. According to an important aspect of the invention, plate 62 has a spherically concave front surface 62S in which a plurality of fiber-supporting bore holes H are drilled to form the above-noted pattern of four concentric rings A, B, C and D. The circular patterns of bore holes H are centered about a center bore hole CH that extends axially through the entire length of stem 62A. Each bore hole H is intended to receive and appropriately position a light-collecting end portion of one of the optical fibers of the fiber optic bundles 33, 34, 37 and 38. Note, the center bore hole CH is not intended to receive an optical fiber and serves only to transmit axial, non-scattered, beam light to the axial light collecting component 32, described below. Each bore hole H has a diameter slightly exceeding the nominal diameter (500 microns) of a single optical fiber it is intended to receive. Preferably, each bore supports the light-collecting end portion of one optical fiber so that (a) the light-collecting end of the supported fiber portion is substantially co-planar with the concave surface 62S, and (b) the longitudinal optical axis of the supported fiber points directly at the anticipated "apparent" position of the light scattering source. i.e., the virtual position of the scattering source taking into account the refractive properties of the transparent rear wall of the flow cell through which scattering is viewed by the light-collecting fiber ends. By this arrangement, scattered light will enter the respective light-collecting ends of the supported fiber portions in a direction substantially parallel to the fiber axes A' and will thereby be most efficiently coupled into the fiber interiors for transmission to the associated photodetectors. As best shown in FIGS. 5A and 5B, the fiber-supporting bore holes H pass completely through plate 62, thereby enabling the fiber ends to enter the bore holes from the rear surface of plate 62 and be suitably fixed to the plate (e.g., by epoxy) so that the light-collecting ends are substantially co-planar with the concave front surface 62S. Preferably, each bore hole H is of a length to provide axial support to the fiber end portion it contains for a distance of at least 2 mm from the fiber's light-collecting end.

Referring to FIG. 5A, plate 62 is shown in a position in which the center of curvature CC of surface 62S is located at the rear surface 10S of the optical flow cell 10. Viewing the flow cell center C (where the scattering source is nominally locate) through the optically transparent (quartz) rear wall RW of the flow cell, the flow cell center C actually appears to be located at a point C', inside the flow cell wall. Thus, in drilling holes H, it is preferred that their respective axes A' (which is coincident with the axes of the supported fibers) converges at point C'. In the preferred embodiment, the radius of curvature of surface 62S is about 0.25 inches, and the apparent position of the flow cell center is about 0.030 inches further away from surface 62S, inside the flow cell wall.

Figure 8:
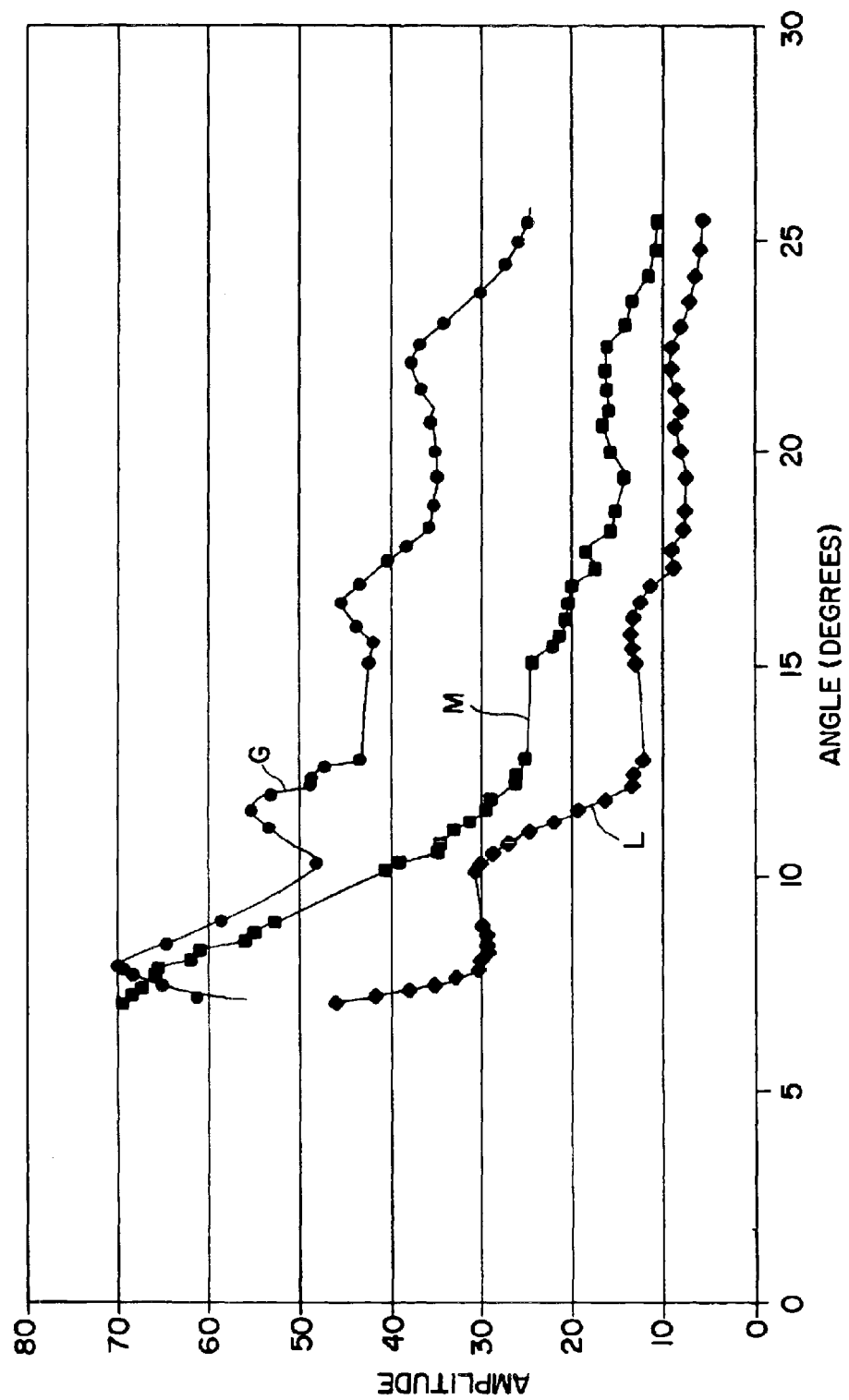
FIG. 8 is a graph plotting the intensity of forward light scatter verses angle for three different white cell types.

As indicated above, each ring of bore holes in surface 62A supports the optical fibers of one of the fiber optic bundles 33, 34, 37 and 38. Thus, referring to FIG. 5B, the twelve bore holes of ring A, for example, support a total of twelve optical fibers, as may constitute the number of fibers of fiber optic bundle 33. Similarly, the thirty-four bore holes of ring D can support a total of 34 fibers, as may constitute the number of fibers in fiber optic bundle 38. Obviously, the diameter of the rings determines the number of optical fibers that can be accommodated. The nominal angle at which forward light scatter is detected is determined by the diameter of each ring, as determined by a centerline passing through the respective axes of the bore holes, and the axial distance of the ring from the scattering source. The angular ranges through which scatter is detected is determined by the diameter of each fiber, assuming there is a single fiber in each bore hole. According to a particularly preferred embodiment of the invention, the diameter of fiber optic rings A, B, C, and D and the radius of curvature of surface 62A are chosen so as to provide nominal forward scatter angles of approximately 11°, 16°, 24° and 32°. Referring to FIG. 8 in which the intensity (amplitude) of forward scatter as a function of angle is plotted for the three major sub-populations of leukocytes (namely, lymphocytes L, monocytes M and granulocytes G), it will be appreciated that the preferred angles of approximately 11°, 16° and 24° provide for a relatively good displacement of the three curves; thus, in a scattergram in which any two of the forward scatter angles are plotted against each other, the three sub-populations of leukocytes will be readily identified. A radius of curvature of about 6.2 mm. for surface 62A, and a fiber diameter of 500 microns provides an angular range, centered about the preferred nominal angles, of about plus or minus 2°.

Figure 6A:
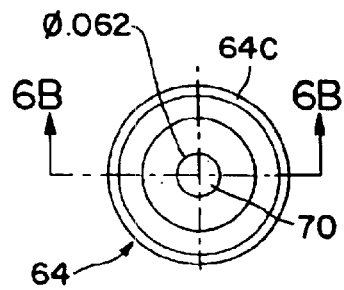
FIGS. 6A and 6B are front plan and cross-sectional views, respectively, of the axial light reflector component of the FIG. 3 apparatus.
Figure 6B:
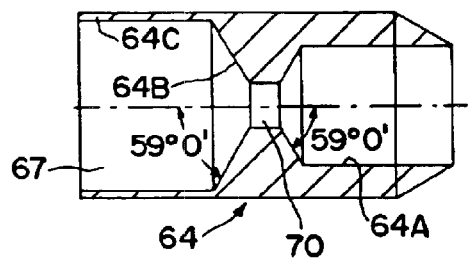
Figure 7A:
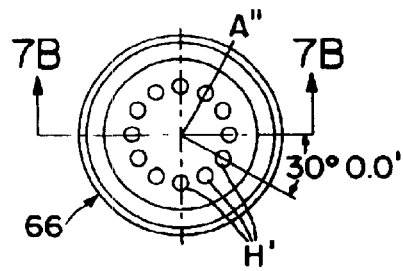
FIGS. 7A and 7B are front plan and cross-sectional views, respectively, of the axial light diffuser/secondary fiber optics holder component of the FIG. 3 apparatus.
Figure 7B:
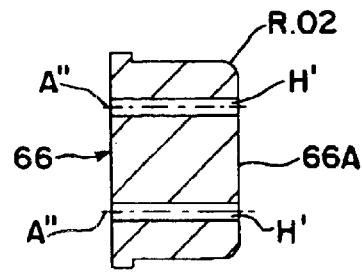

Axial Light Collecting Component:

The axial light collecting component 32 of fiber optic holder 32 operates both to (1) support the respective light-collecting ends of one or more fiber optic bundles in a position to receive axial beam light for transmission to remotely positioned photodetector(s) and (2) prevent such beam light from being retro-reflected back towards the back-scatter detector D' where it would otherwise interfere with the collection and detection of the relatively low-level back-scatter signal. In preventing retro-reflection of beam light, component 32 functions to diffuse the beam light it collects prior to collecting it for transmission and detection. Referring FIGS. 4, 6A and 6B, component 32 comprises a cylindrically-shaped housing 64 having a central, cylindrically-shaped opening 64A in its forward end. The stem portion 62A of plate 62 is press fit into opening 64A and thereby provides support for housing 64. The rear portion of housing 64 has a conically-shaped internal wall 64A having a reflective surface. Wall 64A defines, in part, a light-reflecting chamber 65. A circular flange 64C extending rearwardly from housing 64 defines a cylindrical opening 67 that supports an axial plug 66 (shown in FIGS. 7A and 7B) that serves as a secondary fiber optic holder. A small, centrally located opening 70 in housing 64 provides communication between openings 64 and 67. The axial plug 66 is provided with a planar, light-diffusing top surface 66A, preferably made of Delrin®, a trademark of E. I. Dupont. A circular pattern of bore holes H' is formed in plug 66, such holes being parallel to each other and to the central longitudinal axis A" of the plug. These bore holes are adapted to receive optical fibers, preferably alternating around the circular pattern from either of the fiber optic bundles 35 or 36 shown in FIGS. 1 and 2. The optical fibers from bundles 35 and 36, are positioned within the bore holes H' so that their respective light-collecting ends are co-planar with the light-diffusing surface 66A. Thus, as indicated in FIG. 4, an axial light beam B passing through the central bore hole CH formed in stem 62A and through the central opening 70 in member 64 will strike the light-diffusing surface 66A of plug 66. The incident beam light is thus diffused in all directions, and the diffused light is reflected multiple times within the reflection chamber 65 until a portion of the reflected light strikes the light-collecting ends of the optical fibers supported by plug 66. Axial beam light is thus collected and transmitted to photodetectors PD3 or PD4. Owing to (a) the relatively small diameter (about 1 mm) of the central bore hole CH, (b) the length (about 12 mm) of the central bore hole CH, and (c) the light-diffusing effect of surface 66A, minimal beam light is reflected back towards the optical flow cell and the back-scatter detector D' that might interfere with the detection of both forward and back-scattered light. Preferably, a pair of color absorption filters 40 and 42 is positioned between the light-discharge ends of fiber optic bundles 35 and 36, respectively, and the light-sensitive surfaces of photodetectors PD3 and PD4 for the purpose of differentiating axial light loss at two different wavelengths, e.g. in the event beam B is polychromatic (as is the case when two different lasers are used to irradiate the particles).

Figure 9A:
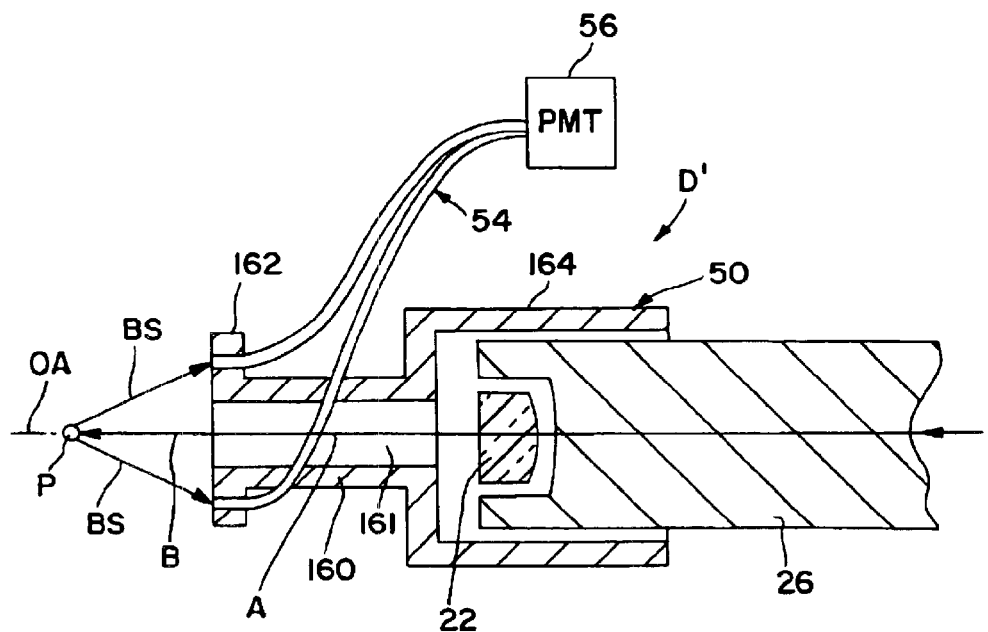
FIGS. 9A and 9B are cross-sectional and front plan views, respectively, of a back-scatter detector comprising the present invention.
Figure 9B:
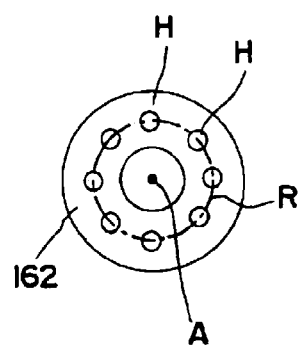

Back-Scatter Detector:

Referring additionally to FIGS. 9A and 9B, the back-scatter detector D' comprises a fiber optic holder 50, a bundle of optical fibers 154 and a photodetector 56. The optical fibers are preferably the same as those described above, and the photodetector 56 is preferably a conventional photomultiplier tube (PMT). The optical fiber holder 50 is preferably made of black plastic, most preferably Delrin plastic, a product of E. I. Du Pont. Holder 50 comprises a relatively tiny central tubular portion 160 having a central bore 61 extending along its entire length. The central tubular potion 160 is provided with a circular, fiber-holding flange 162 at one end, and an enlarged tubular portion 164 at its opposing end. According to a preferred embodiment, the central tubular portion 160 has a length of about 2.5 mm., and an outside diameter of about 1.5 mm. The diameter of bore 161 is about 1.3 mm, sufficiently large to pass the particle-irradiating beam(s) B so that it can irradiate a particle P after passing through the bore. The enlarged tubular portion 164 has a length of about 4.0 mm., an outside diameter of about 3.3 mm. and an inside diameter of about 3.0 mm. The inside diameter of portion 164 is adapted to fit snugly over the end of lens housing 26, whereby the lens housing provides total support for the fiber optic holder.

As best shown in FIG. 9B, the circular flange 162 is provided with a plurality of bore holes H, each having a diameter adapted to receive and retain the light-collecting end portion of an optical fiber of the type described above; thus, each hole H has a diameter slightly exceeding the 500 micron fiber diameter. The bore holes H are arranged in a circular pattern to form a ring R centered about the central longitudinal axis A of the holder 50. Note, in use, axis A is coincident with optical axis OA. Preferably, ring R has a diameter of about 1.75 mm. Based on the anticipated spacing between the end of flange 162 (which is intended to abut the front face 10 A of the flow cell 10) and the scattering source (i.e., the center of flow cell), this ring diameter provides a nominal back-scatter angle of about 7 degrees; and the 500 micron fiber diameter provides an angular range of about 2 degrees (centered about 7 degrees). Thus, the angular range through which back-scatter is collected by the fiber optic bundle 54 is between about 6 and about 8 degrees.

Due to the relatively small area of the respective light-collecting ends of the optical fibers, and the fact that each end preferably points directly at the scatter source (as described below), the fibers collect relatively little stray laser light reflecting from various sources (e.g. the faces of the optical flow cell) located between the forward-scatter detector and the back-scatter detector. Thus, through the use of fibers 56, the signal-to-noise level of photodetector 56 is maintained relatively high compared to the non-directional, large-area prior art detectors that collect, in addition to the back-scatter signal of interest, large amounts of back-scattered light from sources other than the cells of interest.

Figure 10A:
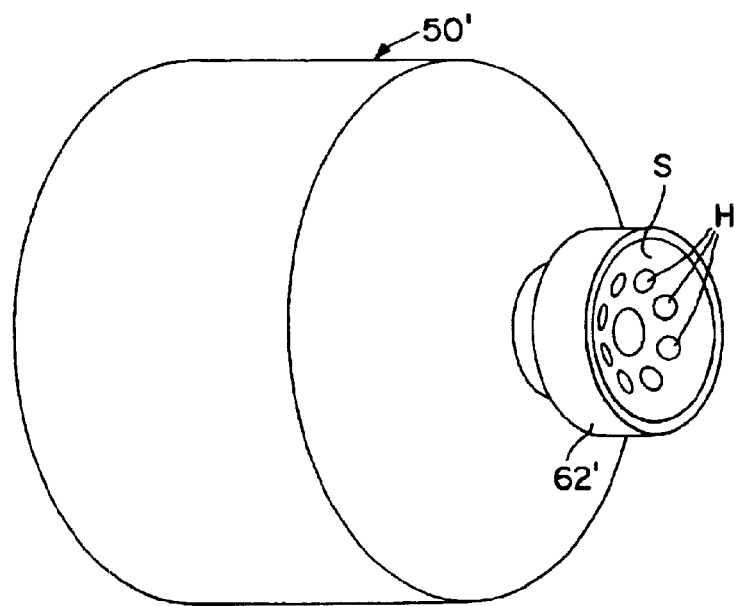
FIGS. 10A and 10B are perspective and cross-sectional illustrations, respectively, of a preferred back-scatter collector.
Figure 10B:
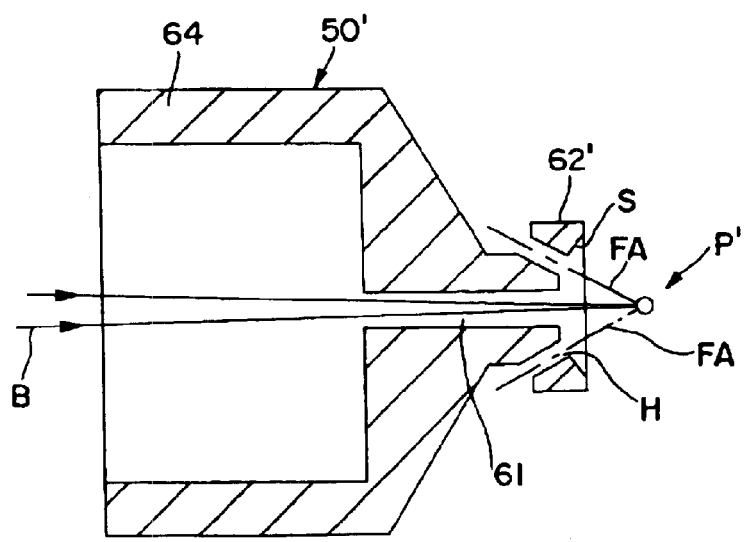

In the embodiment shown in FIG. 9A, it will be seen that the light-collecting end portions of the optical fibers are supported so that each fiber axis FA extends substantially parallel to the axis A of holder 50. In FIGS. 10A and 10B, another, more preferred, embodiment of the invention is shown in which a fiber holder 50' serves to support the fiber end portions so that their respective axes FA converge at the point P' that represents the apparent position of the scattering source, i.e., the virtual position as viewed through the refractive front face of the flow cell. Here, a modified flange 162' is provided in which the fiber-containing bore holes H are formed (drilled) in a spherically-concave surface S. By this arrangement, the back-scattered light from the irradiated particle enters the light-collecting ends of the fibers from a direction that is substantially parallel to the fiber axis FA. Thus, optical losses due to multiple internal reflections within the fibers are reduced. This is especially advantageous in light of the relatively low-intensity back-scatter received from the particles.

As described in the commonly assigned U.S. patent application Ser. No. 10/227,010 entitled "Method and Apparatus for Differentiating Blood Cells Using Back-Scatter," the apparatus of the invention is especially useful in differentiating various blood cells, and especially platelets, on the basis of their respective back-scatter signatures.

The invention has been disclosed with reference to particularly preferred embodiments. It will be appreciated that various modifications can be made without departing from the spirit of the invention, and such modifications are intended to be encompassed by the ensuing claims.

What is claimed is:

1. Apparatus adapted for use in a flow cytometer for detecting light scattered by a small particle or cell comprising a biological liquid, said small particle or cell being irradiated by a light beam as it passes through an optical flow cell of said flow cytometer, said apparatus comprising:
   (a) a plurality of photodetectors;
   (b) a plurality of optical fibers, each optical fiber having a light-collecting end, and having a light-discharge end disposed in close proximity to one of said photodetectors; and
   (c) a pair of fiber optic holders, one holder serving to support the respective light-collecting ends of a first portion of said plurality of optical fibers in a position to receive and collect back-scattered light from an irradiated cell or particle, and the other of said holders serving to support the respective light-collecting ends of a second portion of said plurality of optical fibers in a position to receive and collect forward-scattered light from the same irradiated cell or particle, said other fiber optic holder further serving (a) to support a light-diffusing surface in a position to diffuse axial beam light, as modulated in intensity by a particle or cell passing through said light beam, and (b) to support a third portion of said plurality of optical fibers in a position to receive and collect said axial beam light upon being diffused by said light-diffusing surface.

2. The apparatus as defined by claim 1 wherein each of said optical fibers of said first and second portions is supported so that a segment thereof in the vicinity of said light-collecting end extends towards the irradiated particle.

3. The apparatus as defined by claim 1 wherein the respective light-collecting ends of said optical fibers of said first and second portions are arranged on a spherically concave surface to form one or more circular patterns.

4. The apparatus as defined by claim 3 wherein the respective light-collecting ends of said optical fibers of said first and second portions are arranged on said spherically concave surface to form a plurality of concentric circles, the optical fibers of each circle being adapted to detect light scattered by an irradiated particle or cell within an angular range determined by the diameter of each optical fiber, the respective diameters of said circles and the displacement of said first circles from said irradiated particle or cell.

5. The apparatus as defined by claim 3 wherein the respective light-collecting ends of said third portion of said optical fibers are supported in the vicinity of the center of said circular patterns to collect said axial beam light upon being diffused by said light-diffusing surface.

6. The apparatus as defined by claim 5 wherein said third portion of said optical fibers are supported in a circular pattern centered about the path of said axial light beam.

7. The apparatus as defined by claim 5 wherein each of said optical fibers of said third portion has a central longitudinal axis, and wherein a portion of said optical fibers of said third portion is supported in the vicinity of its respective light-collecting end so that the longitudinal axes of said supported portions extend substantially parallel to each other.

8. The apparatus as defined by claim 1 wherein said other fiber optic holder defines a reflection chamber positioned to reflect diffused axial beam light towards the respective light-collecting ends of said third portion of optical fibers.

9. The apparatus as defined by claim 1 wherein said other fiber optic holder defines an elongated bore hole positioned to transmit axial beam light to said light-diffusing surface, said bore hole being of a length and diameter to restrict the passage of diffused axial light back towards the respective light-collecting ends of optical fibers supported by said one fiber optic holder.

* * * * *